United States Patent
Satake

(10) Patent No.: US 9,387,310 B2
(45) Date of Patent: Jul. 12, 2016

(54) BALLOON CATHETER SYSTEM

(75) Inventor: Shutaro Satake, Kamakura (JP)

(73) Assignee: Japan Electel Inc. (JP)

(*) Notice: Subject to any disclaimer, the term of this patent is extended or adjusted under 35 U.S.C. 154(b) by 0 days.

(21) Appl. No.: 14/117,665

(22) PCT Filed: Jul. 5, 2012

(86) PCT No.: PCT/JP2012/067239
§ 371 (c)(1),
(2), (4) Date: Nov. 14, 2013

(87) PCT Pub. No.: WO2014/006730
PCT Pub. Date: Jan. 9, 2014

(65) Prior Publication Data
US 2015/0148742 A1 May 28, 2015

(51) Int. Cl.
*A61B 18/12* (2006.01)
*A61M 25/10* (2013.01)
*A61B 18/04* (2006.01)
(Continued)

(52) U.S. Cl.
CPC .......... *A61M 25/10182* (2013.11); *A61B 18/04* (2013.01); *A61B 18/1492* (2013.01); *A61M 25/10181* (2013.11); *A61M 25/10185* (2013.11); *A61M 29/02* (2013.01); *A61B 2018/0019* (2013.01); *A61B 2018/0022* (2013.01); *A61B 2018/00642* (2013.01); *A61B 2018/00702* (2013.01); *A61B 2018/00791* (2013.01); *A61B 2018/046* (2013.01); *A61M 25/1006* (2013.01); *A61M 2025/0004* (2013.01); *A61M 2025/1068* (2013.01); *A61M 2025/1084* (2013.01); *A61M 2210/125* (2013.01); *A61M 2210/127* (2013.01)

(58) Field of Classification Search
CPC ............... A61B 17/12136; A61B 2017/22051; A61B 2017/22067; A61B 2017/34; A61B 2017/3486; A61B 2018/022; A61M 2025/102; A61M 2025/1022; A61M 2025/1025; A61M 2025/1061
See application file for complete search history.

(56) References Cited

U.S. PATENT DOCUMENTS 2,734,508 A * 2/1956 Kozinski ................. A61F 7/123
219/229
5,571,153 A * 11/1996 Wallsten ................ A61B 18/08
604/114

(Continued)

FOREIGN PATENT DOCUMENTS

JP 2003-102850 A 4/2003
JP 2005-177293 A 7/2005
(Continued)

*Primary Examiner* — Ronald Hupczey, Jr.
(74) *Attorney, Agent, or Firm* — Akerman LLP

(57) ABSTRACT

A balloon catheter system enabling balloon stretching and deflating, and balloon stretch-releasing and inflating operations to be performed at a time with a single operation. The system includes a catheter shaft including outer and inner tubes slidable to each other and a deflatable/inflatable balloon arranged between the distal ends thereof. A solution transport path is formed between the outer and inner tubes. Anterior and posterior tanks are arranged in a handle. The tanks and the inner tube passing through the central portion thereof are slidable to each other. Stopcocks are mounted in sliding portions between the inner tube and these tanks. These tanks are connected to the inside of the balloon via the solution transport path. A piston is provided inside the posterior tank. Thus, the inner pressures of these tanks change by reciprocating the inner tube fixed to the piston, thus simplifying balloon deflating and inflating operations.

22 Claims, 5 Drawing Sheets

(51) Int. Cl.
 *A61B 18/14* (2006.01)
 *A61M 29/02* (2006.01)
 *A61B 18/00* (2006.01)
 *A61M 25/00* (2006.01)

(56) References Cited

U.S. PATENT DOCUMENTS

| | | | | |
|---|---|---|---|---|
| 6,952,615 B2* | 10/2005 | Satake | ............... | A61B 18/1492 604/113 |
| 8,226,637 B2* | 7/2012 | Satake | ................... | A61B 18/04 604/509 |
| 8,231,617 B2* | 7/2012 | Satake | ................... | A61B 18/04 606/1 |
| 8,821,485 B2* | 9/2014 | Heberer | ................ | A61B 18/02 606/21 |
| 2002/0045854 A1* | 4/2002 | Royo | ................ | A61M 25/1018 604/97.03 |
| 2012/0059368 A1* | 3/2012 | Takaoka | ............. | A61B 18/1492 606/33 |

FOREIGN PATENT DOCUMENTS

| | | |
|---|---|---|
| JP | 2006-198209 A | 8/2006 |
| WO | 2010/070766 A1 | 6/2010 |

\* cited by examiner

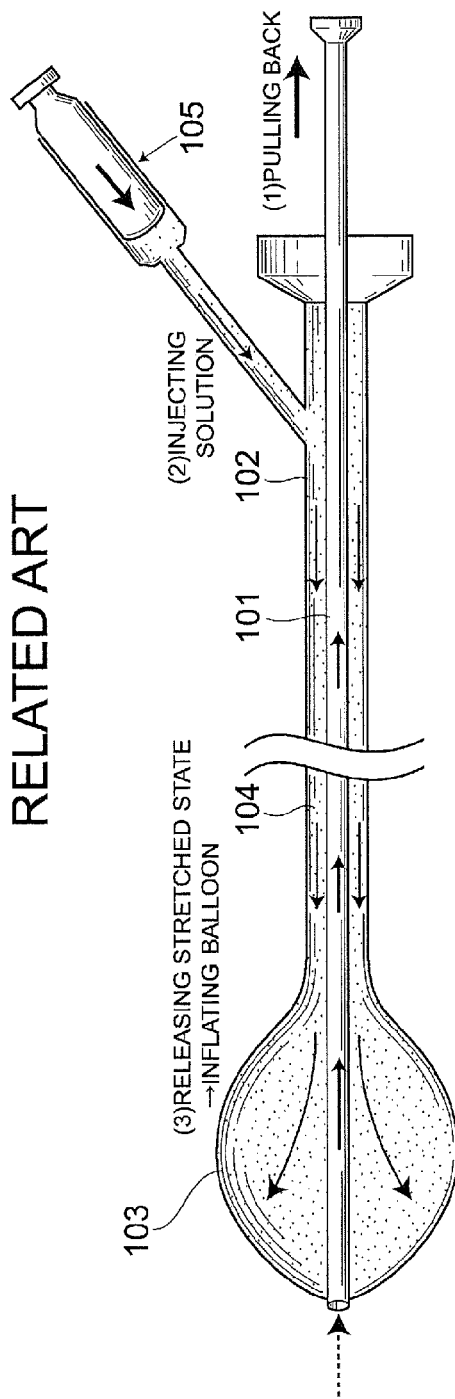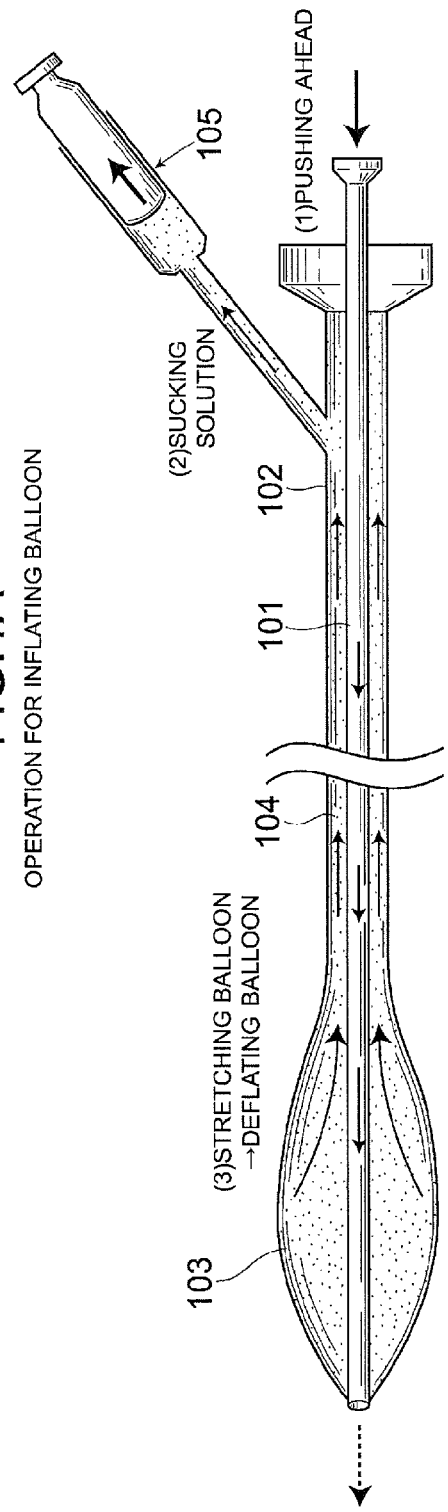

BALLOON CATHETER SYSTEM

This application is a national phase of PCT/JP2012/067239, filed Jul. 5, 2012, the entire contents of which is hereby incorporated by reference.

TECHNICAL FIELD

The present invention relates to a balloon catheter system which is inserted into a luminal organ when in use, and provided with a balloon capable of being inflated and deflated.

BACKGROUND ART

In a balloon catheter to be inserted into a blood vessel or the like, when the balloon is large-sized relative to a diameter of the blood vessel, the balloon is not able to be folded even if a stretchable material is used as a balloon membrane, thus leading to difficulties in inserting the balloon into the blood vessel or the like. For this reason, one has ever devised such a method that an inside of a balloon arranged on distal ends of outer and inner tubes is suctioned while stretching the balloon through a sliding operation between the outer and inner tubes to thereby deflate the balloon into a small size and then the balloon is inserted into the blood vessel until it is allowed to reach and stay at a target site, then followed by injecting a solution or the like into the balloon to inflate the balloon while releasing the stretched state of the balloon. (e.g., see patent document 1, etc.).

One example of such device is shown in FIG. 1. In this drawing, numeral symbol 101 denotes an inner tube, and 102 denotes an outer tube. A stretchable balloon 103 is provided between the distal ends of the inner tube 101 and the outer tube 102. A solution transport path 104 in communication with an inside of the balloon 103 is formed between the inner tube 101 and the outer tube 102. Then, there is provided a syringe 105 that is in communication with the solution transport path 104 to inject a solution into or suction the same from the balloon 103. The inner tube 101 and the outer tube 102 define a shaft 106 of a balloon catheter.

As shown in FIG. 1 (A), when inflating the balloon 103, i) the inner tube 101 is pulled back toward a rear end of the shaft 106, ii) a solution is then injected into the balloon 103 by operating the syringe 105, thereby iii) performing a sequence of operations from releasing the stretched state of the balloon to inflating the balloon.

Also, as shown in FIG. 1(B), when deflating the balloon 103, i) the inner tube 101 is pushed out toward a front end of the shaft 106, ii) the solution inside the balloon 103 is suctioned by operating the syringe 105, thereby iii) performing a sequence of operations from stretching the balloon to deflating the balloon.

As described above, there was conventionally a need to perform the operation for stretching the balloon and the operation for suctioning the inside of the balloon 103 separately from each other in stages; and the operation for releasing the stretched state of the balloon and the operation for inflating the balloon 103 also needed to be separately performed in stages. In either case, therefore, it has taken a lot of trouble and time.

PRIOR ART DOCUMENT

Patent Document

Patent document 1: International publication No. 2010/070766

DISCLOSURE OF THE INVENTION

Problems to be Solved by the Invention

As described above, when employing the conventional method, the operations for stretching and deflating the balloon 103 as well as the operations for releasing the stretched state of the balloon 103 and inflating the same had to be performed in stages by two different sequences of operations. Accordingly, the operations are complicated and an amount of time required for such operations cannot be reduced, thus increasing a burden on a patient as well.

In view of the problems described above, therefore, it is an object of the present invention to provide a balloon catheter system for enabling the operations for stretching and deflating a balloon and the operations for releasing the stretched state of the balloon and inflating the balloon to be performed at a time by a single operation, respectively.

Means for Solving the Problem

In order to attain the above object, a first aspect of the present invention is a balloon catheter system comprising:

a catheter shaft including an outer tube and an inner tube, the outer and inner tubes being slidable to each other;

an inflatable and deflatable balloon arranged between a distal end of the outer tube and a vicinity of a distal end of the inner tube;

a solution transport path formed between the outer tube and the inner tube, in communication with an inside of the balloon;

two, respectively anterior and posterior tanks arranged in a handle of a catheter, in communication with each other via a connecting pipe, the anterior and posterior tanks being slidable relative to the inner tube passing through central portions thereof;

leakproof packing members arranged on sliding portions between the inner tube and the anterior and posterior tanks, the anterior and posterior tanks being allowed to communicate with an inside of the balloon via the solution transport path; and a piston provided inside a front section of the posterior tank to allow inner pressures of the tanks to be changed by a reciprocating movement of the inner tube fixed to a central portion of the piston, wherein the balloon catheter system is configured such that pushing the inner tube forward allows the balloon to be stretched so that an inside of the posterior tank is subjected to a negative pressure to thereby deflate the balloon, while pulling the inner tube backward allows the stretched state of the balloon to be released so that the inside of the posterior tank is subjected to a positive pressure to thereby inflate the balloon.

A second aspect of the present invention is a balloon catheter system wherein in the balloon catheter system according to the first aspect, the balloon is made from a resin rich in elasticity, taking the form of a rotating body.

A third aspect of the present invention is a balloon catheter system wherein in the balloon catheter system according to the first or second aspect, the piston provided movably inside the posterior tank in the handle is connectable to a slide knob arranged above the handle, and the slide knob is movable by a finger.

A fourth aspect of the present invention is a balloon catheter system wherein in the balloon catheter system according to any one of the first to third aspects, a syringe barrel is attached to the connecting pipe via a T shape stopcock.

A fifth aspect of the present invention is a balloon catheter system wherein in the balloon catheter system according to any one of the first to fourth aspects, a stopcock is provided on respective proximal end portions of the anterior and posterior tanks A sixth aspect of the present invention is a balloon catheter system wherein in the balloon catheter system according to any one of the first to fifth aspects, an electrode for delivery of a radiofrequency current and a temperature sensor are provided inside the balloon, while a radiofrequency energy is delivered from a radiofrequency generator through a lead wire inside the catheter shaft and at the same time that vibration waves are transmitted from a vibration generator via the solution transport path to thereby agitate the solution inside the balloon.

A seventh aspect of the present invention is a balloon catheter system wherein in the balloon catheter system according to any one of the first to sixth aspects, the balloon is wire-reinforced so that inflating the balloon enables a mitral or aortic stenosis to be dilated.

Effects of the Invention

Heretofore, the operation for stretching the balloon and the operation for suctioning the solution inside the balloon, and the operation for releasing the stretched state of the balloon and the operation for filling the balloon with the solution are performed separately in stages and hence a lot of trouble and skill is required for the operations. In the first aspect of the present invention, however, when pushing ahead the inner tube relative to the outer tube, the balloon is stretched and at the same time the posterior tank becomes subjected to negative pressure to thereby make the anterior tank, in communication with the posterior tank via the connecting pipe, also subjected to negative pressure, so that the solution inside the balloon is suctioned to deflate the balloon. Contrarily, when pulling back the inner tube relative to the outer tube, the stretched state of the balloon is released and at the same time the posterior tank becomes subjected to positive pressure to thereby make the anterior tank also subjected to positive pressure, so that the balloon is filled with the solution to be inflated. As a result, the operation of the balloon is made easy. Accordingly, such a balloon catheter can be provided that the operations for stretching and deflating the balloon, and the operations for releasing the stretched state of the balloon and inflating the balloon can be practiced at a time with a single operation. Consequently, the amount of time required for handling skill can be shortened and a burden on a patient can be reduced.

According to the second aspect of the present invention, as long as the balloon takes the form of a rotating body, the balloon can be applied to the present system and hence the balloon is applicable to a variety of applications.

According to the third aspect of the present invention, the piston movable inside the posterior tank can be operated by operating a terminal portion connected to the inner tube. Hitherto, the operation of the piston takes a lot of trouble since a way for holding the handle is required to change. According to the invention of the third aspect, however, the piston can be operated using the slide knob above the handle and hence handling skill is speeded up to reduce the amount of time required.

According to the fourth aspect of the present invention, the T shape stopcock is switched if needed and thus the fine regulation of an amount of the solution inside the balloon becomes possible by the syringe barrel. Hence, the balloon is allowed to be in closer contact with a target organ.

According to the fifth aspect of the present invention, utilizing stopcocks is put to use in regulating the piston and performing air-breeding actions inside the anterior and posterior tanks.

According to the sixth aspect of the present invention, since the vibration waves from the vibration generator travel through the solution transport path, the inside of the balloon is agitated, while, since radiofrequency energy from the radiofrequency generator is delivered to the electrode for delivery of radiofrequency current via the lead wire, the balloon is uniformly heated to enable an ablation treatment to be performed. Accordingly, even a less skilled medical doctor can perform the ablation treatments of abnormal cardiac rhythm and cardiac valvuloplasty, simply and in a short amount of time.

According to the seventh aspect of the present invention, when dilating a target organ by the balloon, troubles such as the burst of the balloon or the like can be prevented. Hence, even a less skilled medical doctor can perform cardiac valvuloplasty, simply and in a short amount of time.

BRIEF DESCRIPTION OF THE DRAWING

FIG. 1 is an explanatory drawing showing a structure of a major part of a conventional balloon catheter system and its usage state, in which 1(A) shows a usage state when a balloon is being inflated, while 1 (B) shows a usage state when the balloon is being deflated.

MODE FOR CARRYING OUT THE INVENTION

Nest is a detailed description of a balloon catheter system proposed by the present invention with reference to the accompanying drawings.

Figure 2A:
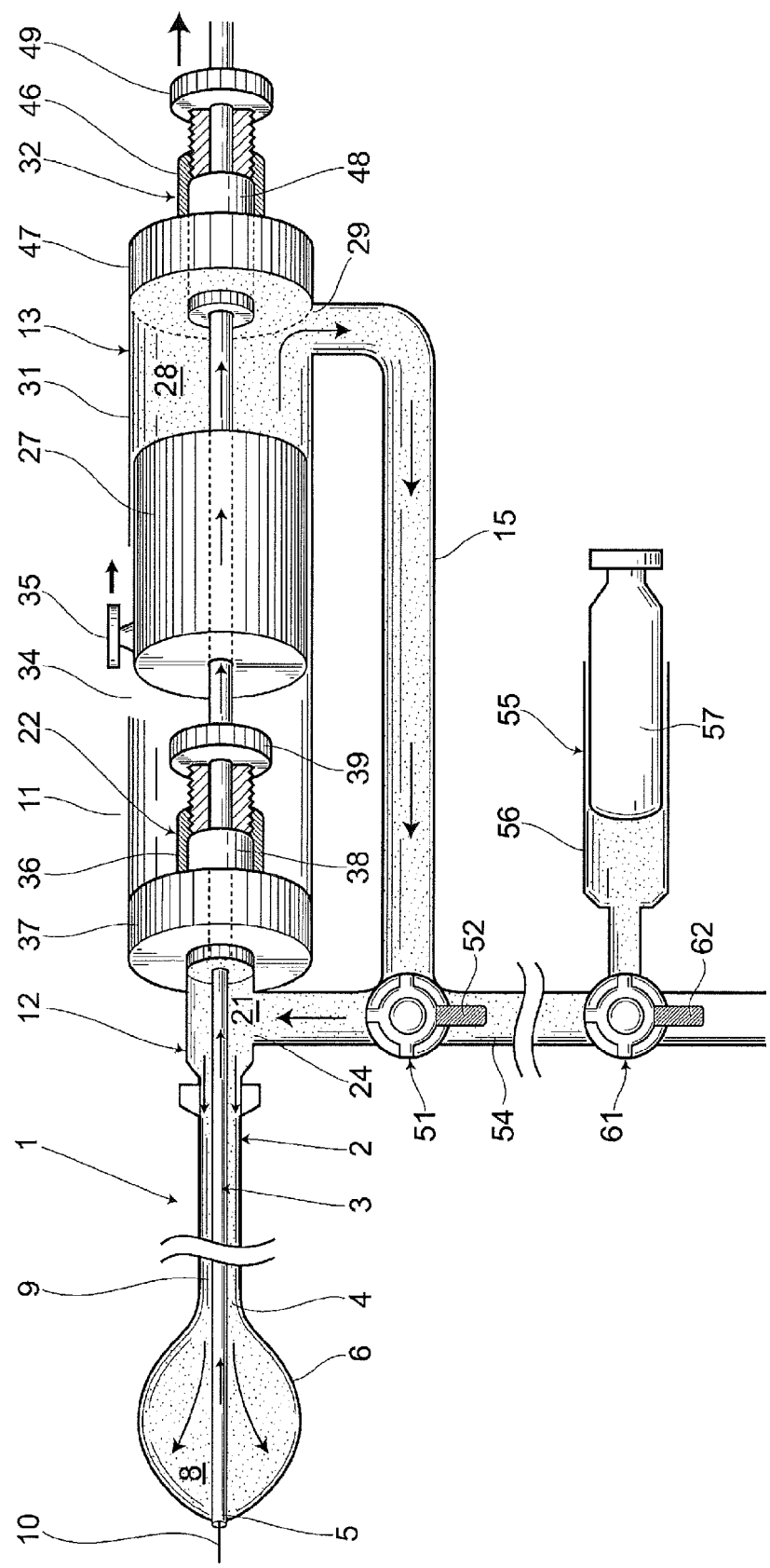
FIG. 2a is an explanatory drawing showing the structure of the major part of the balloon catheter system according to the present invention and its usage state when the balloon is inflated.
Figure 2B:
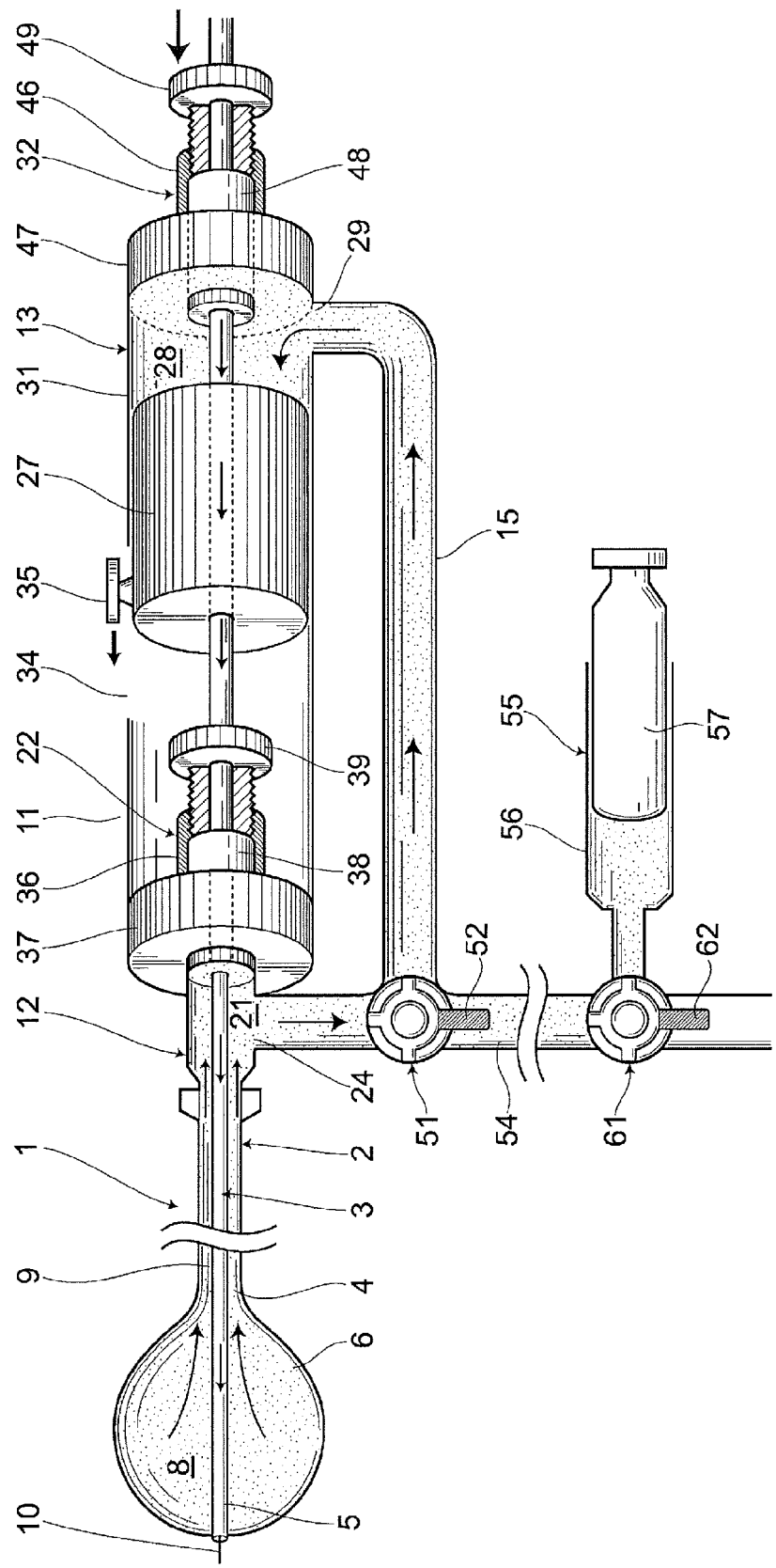
FIG. 2b is an explanatory drawing showing the structure of the major part of the balloon catheter system according to the present invention and its usage state when the balloon is deflated.
Figure 3:
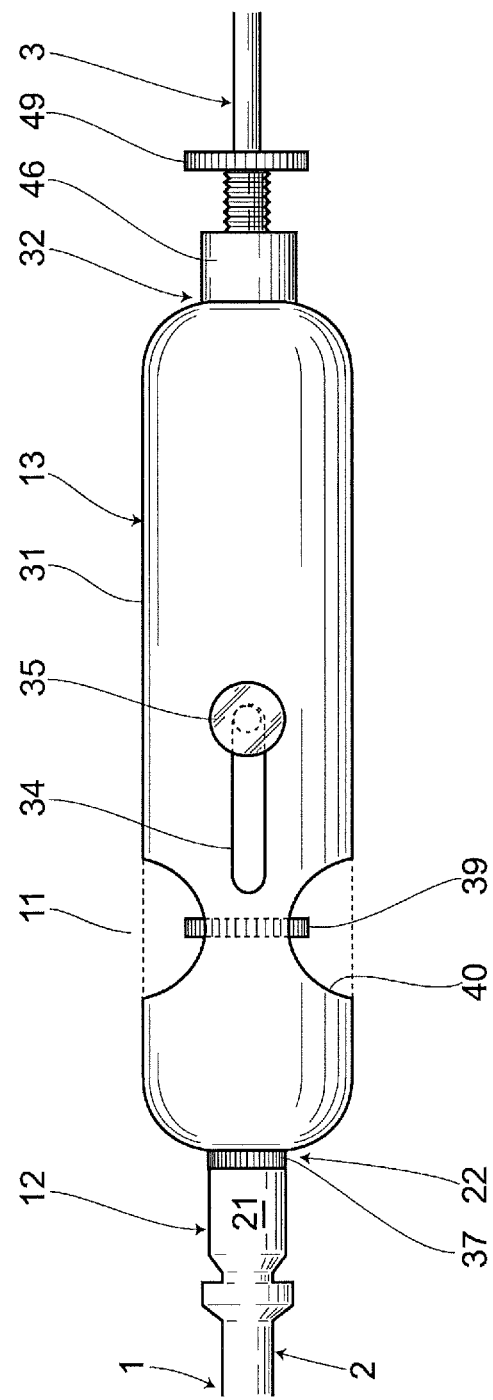
FIG. 3 is a plane view of a handle in FIG. 2b.

FIG. 2a, FIG. 2b and FIG. 3 show a structure of a major part of the balloon catheter system according to one embodiment of the present invention. In the drawings, numeral symbol 1 denotes a cylindrical catheter shaft that is rich in elasticity and insertable into a luminal organ. The catheter shaft 1 comprises an outer tube 2 and an inner tube 3 which are longitudinally slidable to each other. A deflatable and inflatable balloon 6 with an outer surface externally exposed is provided between a distal end 4 of the outer tube 2 and a vicinity of a distal end 5 of the inner tube 3. The balloon 6 is formed into a membrane form, from heat-resistant resin such as polyurethane, PET (polyethylene terephthalate) or the like. The balloon 6 is allowed to inflate in the form of a rotating body such as a substantially spherical form by filling a solution (normally, a mixture of physiological saline and a contrast agent) in the balloon 6.

Between the outer tube 2 and the inner tube 3 inside the catheter shaft 1, there is formed a solution transport path 9 communicating with a filling portion 8 formed inside the balloon 6 to deliver the solution and transmit vibration waves, to the filling portion 8. Numeral symbol 10 denotes a guide wire which guides the balloon section 8 to a target site and is provided in such a manner as to penetrate the inner tube 3.

Anterior and posterior tanks 12, 13, acting as front and rear two solution storage tanks, having their central portions penetrated by the inner tube 3, are arranged tandemly in a handle 11 located at a proximal portion of the catheter shaft 1. The anterior tank 12 includes therein an anterior chamber 21 that communicates with the solution transport path 9 and contains therein a certain amount of the solution. A stopcock 22 for preventing the leakage of solution is arranged in a proximal portion of the anterior chamber 21. A connecting opening 24 connected to one end of a connecting pipe 15 is formed in a lateral portion of the anterior chamber 21.

On the other hand, a piston 27, which is rich in elasticity and made from a material such as rubber, is provided inside a front section of the posterior tank 13. A posterior chamber 28 containing a certain amount of the solution is formed at the rear of the piston 27. A connecting opening 29 connected to the other end of the connecting pipe 15 is formed in a lateral portion of the posterior chamber 28 provided inside the posterior tank 13. Then, the inner tube 3 is fixedly provided in the central portion of the piston 27 so that the change in inner pressure of the posterior chamber 28 inside the posterior tank 13 that occurs in association with the reciprocating movement of the inner tube 3 may be transmitted to the anterior tank 12 through the U-shaped connecting pipe 15 that connects the anterior tank 12 and the posterior tank 13 together.

Going into more detail about the structure of the handle 11, the anterior tank 12 and the posterior tank 13, and the inner tube 3 passing through the central portions of these tanks 12, 13 are provided slidably relative to each other, while in the posterior tank 13, the above-described piston 27 is provided slidably together with the inner tube 3, inside the cylinder 31 with both ends thereof opened. In the sliding portion between the inner tube 3 and the posterior tank 13 located at both ends of the cylinder 31, there is provided, in addition to the aforesaid stopcock 22, another stopcock 32 acting as a packing member for preventing the solution from leaking. As shown in FIG. 3, on an upper surface of the cylinder 31, there is formed an elongated hole 34 extending along the traveling direction of the piston 27. On an outer surface of the piston 27 opposed to the elongated hole 34, there is provided a slide knob 35 arranged above the handle 11 in a manner capable of being connected thereto. The side knob 35 is formed into such a shape as to enable an operator to move the piston 27 using a finger.

The stopcock 22 comprises a cap 37 for closing a rear end of an opening of the anterior tank 12 and including a tubular portion 36 protruding toward a rear end, a rubber member 38 serving as a packing member fitted into the tubular portion 36, and a plug 39 screwed into an opening of the tubular portion 36. The inner tube 3 is provided so as to penetrate the centers of these cap 37, rubber member 38 and plug 39 in a manner slidable therethrough. Further, in an anterior region of the cylinder 31, there is formed a cutout hole 40 corresponding to the plug 39, thus making it possible to turn the plug 39 with a finger through the cutout hole 40. Accordingly, by turning the plug 39 in one direction to let the rubber member 38 undergo compression deformation within the tubular portion 36, the rubber member 38 and an outer surface of the inner tube 3 are allowed to come into more intimate contact with each other, thereby preventing the air and solution from leaking from the anterior chamber 21, while making the inner tube 3, eventually the piston 27, less likely to slide. Contrarily, by turning the plug 39 reversely to relax the compressed and deformed state of the rubber member 38, the rubber member 38 and the outer surface of the inner tube 3 are allowed to come into less intimate contact with each other, thereby making the air and solution easier to be evacuated from the anterior chamber 21, while making the inner tube 3, eventually the piston 27 easier to slide.

In a similar fashion, the stopcock 32 comprises a cap 47 for closing a rear end of an opening of the posterior tank 13 and including a tubular portion 46 protruding toward a rear end, a rubber member 48 that is rich in elasticity and serves as a packing member fitted into the tubular portion 46, and a plug 49 screwed into an opening of the tubular portion 46. The inner tube 3 is provided so as to penetrate the centers of these cap 47, rubber member 48 and plug 49 in a manner slidable therethrough. The plug 49 is arranged behind the posterior tank 13 and exposed to the outside. By turning the plug 49 in one direction to let the rubber member 48 undergo compression deformation within the tubular portion 46, the rubber member 48 and the outer surface of the inner tube 3 are allowed to come into more intimate contact with each other, thereby preventing the air and solution from leaking from the posterior chamber 28, while making the inner tube 3, eventually the piston 27, less likely to slide. Contrarily, by turning the plug 49 reversely to relax the compressed and deformed state of the rubber member 48, the rubber member 48 and the outer surface of the inner shaft 3 are allowed to come into less intimate contact with each other, thereby making the air and solution easier to be evacuated from the posterior chamber 28, while making the inner tube 3, eventually the piston 27 easier to slide.

Two connecting openings of a T shape stopcock 51 are connected to the connecting pipe 15 at a certain position in a flow path thereof, while a syringe 55 is connected to the remaining one connecting opening of the T shape stopcock 51 via the solution transport pipe 54. Further, two connecting openings of another T shape stopcock 61 are connected to a certain portion between the solution transport pipe 54 and the syringe 55, while a vibration generator 71 (see FIG. 4) is connected to the remaining one connecting opening of the T shape stopcock 54. An operational piece 52 turnable with a finger is provided in the T shape stopcock 51. By operating the operational piece 52, either one of the posterior chamber 28 and the solution transport pipe 54 is allowed to communicate with the anterior chamber 21 leading to the solution transport pipe 9. Also, an operational piece 62 turnable with a finger is provided in a T shape stopcock 61, and by operating the operational piece 62, either one of the syringe 55 and solution transport pipe 54 is allowed to communicate with the solution transport pipe 54 leading to the T shape stopcock 51.

The syringe 55 acting as a solution injector comprises a tubular body 56 connected to the T shape stopcock 61 and a movable plunger 57. When the plunger 57 is pushed with the anterior chamber 21 and the solution transport pipe 54 being allowed to communicate with each other by the T shape stopcock 51, and the solution transport pipe 54 and the syringe 55 being also allowed to communicate with each other by the T shape stopcock 61, then the solution inside the tubular body 56 is allowed to pass from the solution transport pipe 54 through the anterior chamber 21 and the solution transport path 9 in sequence to thereby be supplied to the inside of the balloon 6. Contrarily, when the plunger 57 is pulled back, then the solution inside the balloon 6 is allowed to pass from the solution transport path 9 through the anterior chamber 21 and the transport pipe 54 in sequence to thereby be recovered to be back inside the tubular body 56.

Then, as shown in FIG. 2a, when the inner tube 3 is pulled back after filling, with the solution, the insides of the anterior tank 12 and the posterior tank 13, the connecting pipe 15 and the solution transport path 9, with the anterior chamber 21 and the posterior chamber 28 being allowed to communicate with each other by the T shape stopcock 51, then the stretched state of the balloon 6 is released and at the same time the inner pressure of the posterior tank 13 becomes higher due to the backward movement of the piston 27 and the inner pressure of the anterior tank 12 also becomes higher via the connecting pipe 15, to thereby fill the inside of the balloon 6 with the solution through the solution transport path 9, thus inflating the balloon 6. On this occasion, since the inner tube 3 is fixed to the piston 27, the balloon 6 can be easily inflated by gripping the posterior tank 13, acting as a handle, with a left hand and pulling the slide knob 35 attached to the piston 27 with a right hand.

As shown in FIG. 2b, when the inner tube 3 is pushed out after filling, with the solution, the insides of the anterior tank 12 and the posterior tank 13, the connecting pipe 15 and the solution transport path 9, with the anterior chamber 21 and the posterior chamber 28 being allowed to communicate with each other by the T shape stopcock 51, then the balloon 6 is stretched and at the same time the piston 27 advances to allow the inside of the posterior tank 13 to be subjected to negative pressure so that the inside of the anterior tank 12 also becomes subjected to negative pressure via the connecting pipe 15, to thereby suction the solution inside the balloon 6 via the solution transport path 9, thus deflating the balloon 6. Accordingly, in this case, the balloon 6 can be easily deflated by pushing out the slide knob 36.

As described above, according to the balloon catheter system thus structured, when the inner tube 3 is pushed out, the balloon 6 is stretched and at the same time the piston 27 advances to allow the posterior chamber 28 inside the posterior tank 13 to be subjected to negative pressure so that the anterior chamber 21 inside the anterior tank 12 becomes also subjected to negative pressure via the connecting pipe 15, to thereby suction the solution inside the balloon 6, thus permitting the balloon 6 to be deflated. Contrarily, when the inner tube 3 is pulled back, the stretched state of the balloon 6 is released and at the same time the piston 27 moves backward to allow the posterior chamber 28 inside the posterior tank 13 to be subjected to positive pressure, so that the anterior chamber 21 inside the anterior tank 12 becomes also subjected to positive pressure via the connecting pipe 15 to thereby increase the solution inside the balloon 6, thus permitting the balloon 6 to be inflated.

In other words, if the anterior tank 12 were an only tank, the operation for pushing out the inner tube 3 would become an operation for pushing out, by the piston 27, the solution inside the anterior tank 12 toward the balloon 6 to thereby urge the balloon 6 to stretch and yet inflate. Contrarily, the operation for pulling back the inner tube 3 would become an operation for recovering, by the piston 27, the solution inside the balloon 6 to be back into the inside of the anterior tank 12 to thereby release the stretched state of the balloon 6 and yet deflate the balloon 6. Therefore, each operation would result in the contradictory movement. According to the present embodiment, however, the two tanks, i.e., the anterior and posterior tanks 12, 13 are connected to each other, and thus, the operation for pushing out the inner tube 3 urges the balloon 6 to stretch and deflate, and contrarily, the operation for pulling back the inner tube 3 urges the balloon 6 to release its stretched state and inflate, thus achieving a non-contradictory coordinated movement.

Accordingly, stretching and deflating the large-size balloon 6 or releasing the stretched state of the balloon 6 and inflating the same can be achieved with a single operation, thus simplifying the operations, enabling the time required for manual operations to be shortened, thus reducing burdens on a patient.

Figure 4:
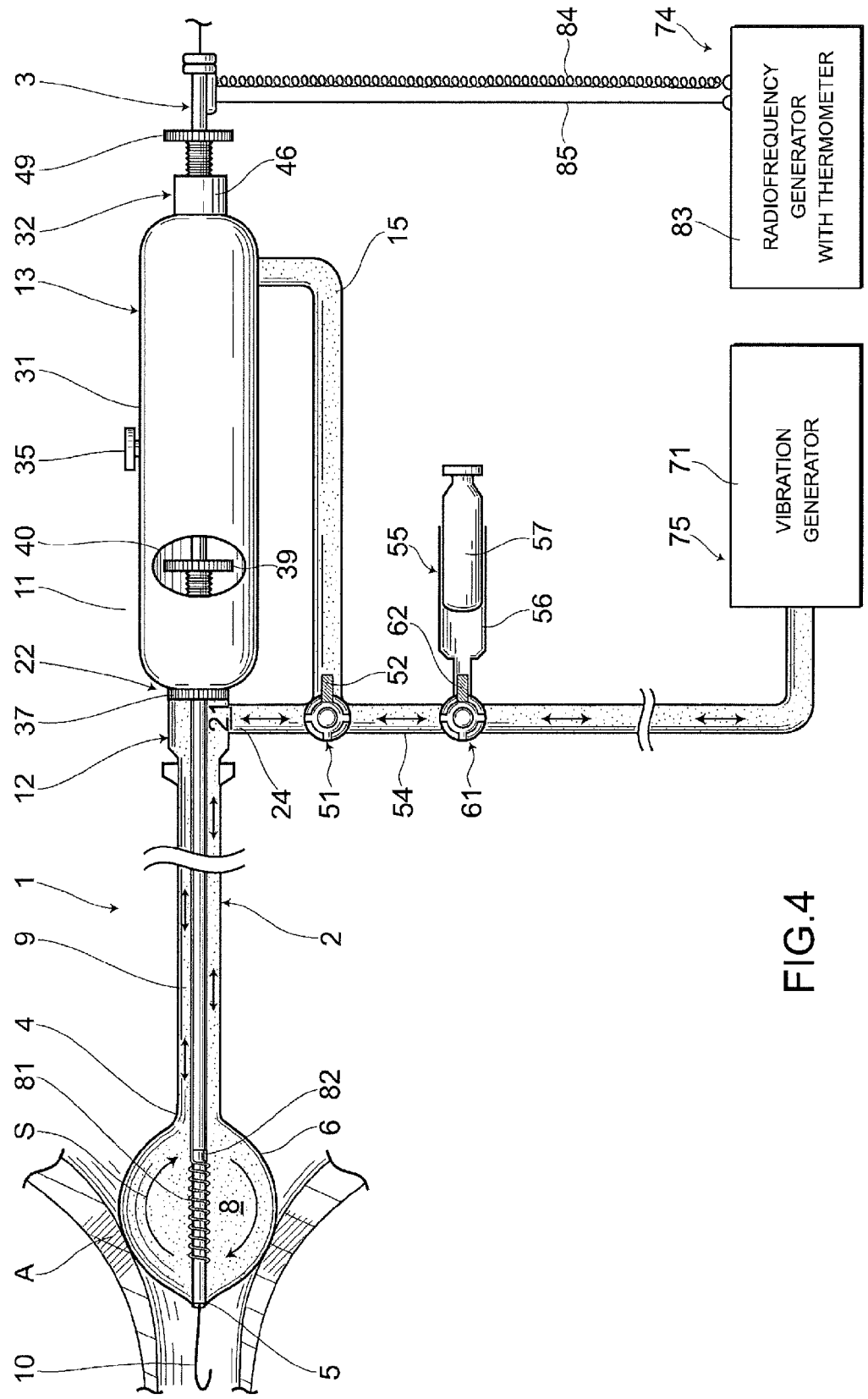
FIG. 4 shows an explanatory drawing of the structure of the major part of the balloon catheter system according to a first working example (ablation of an ostium of the pulmonary vein) of the present invention and its usage state.

Next is a detailed description of an example in which the balloon catheter system thus structured is applied to an ablation of an ostium of a pulmonary vein with reference to FIG. 4 as an accompanying drawing. The balloon catheter system shown in FIG. 4 is one where a radiofrequency current delivery device 74 and an in-balloon agitation device 75 are incorporated into the structure of the embodiment described above.

The radiofrequency current delivery device 74 comprises an electrode 81 for delivery of radiofrequency current and a temperature sensor 82 which are provided inside the balloon 6; a radiofrequency generator 83 with a thermometer which is provided outside the catheter shaft 1; a lead wire 84 for electrically connecting the electrode 81 for delivery of radiofrequency current and the radiofrequency generator 83 with each other; and another lead wire 85 for electrically connecting the temperature sensor 82 and the radiofrequency generator 83 with each other. The electrode 81 for delivery of radiofrequency current is wound around the inner tube 3 in a coiled manner to act as an electrode for heating the inside of the balloon 6. Further, the electrode 81 for delivery of radiofrequency current has a single-electrode structure to perform radiofrequency current delivery between itself and a counterpart electrode (not shown) provided outside the catheter shaft 1. The electrode 81 for delivery of radiofrequency current produces heat due to energization caused by the delivery of radiofrequency current. Alternatively, the electrode 81 for delivery of radiofrequency current may have two electrodes to perform radiofrequency current delivery between both the electrodes.

Also, inside the balloon 6, there is provided the temperature sensor 82 fixed on a proximal end side of the inner tube 3 in contact with the electrode 81 for delivery of radiofrequency current to detect the temperature of the electrode 81 for delivery of radiofrequency current. In addition, although not shown in the present embodiment, in addition to the temperature sensor 82, another temperature sensor for detecting the temperature inside the balloon 6 may be fixed to the vicinity of the distal end 5 of the inner tube 3. For more information on such additional temperature sensor, see the patent document 1.

The radiofrequency generator 83 supplies radiofrequency energy, being an electric power, to the electrode 81 for delivery of radiofrequency current to heat the balloon 6, and is equipped with a thermometer (not shown) for measuring the temperature of the electrode 81 for delivery of radiofrequency current, eventually the temperature inside the balloon 6 by means of a detection signal transmitted from the temperature sensor 82 via the lead wire 85 to thereby indicate the temperature inside the balloon 6. Further, the radiofrequency generator 83 is configured to successively import temperature information measured by the thermometer to determine the radiofrequency current energy to be supplied to the electrode 81 for delivery of radiofrequency current through the lead wire 84. The lead wires 84, 85 are fixed along the inner tube 3 over an entire axial length of the inner tube 3.

The in-balloon agitation device 75 is constituted by connecting the vibration generator 71 to the solution transport pipe 54. The vibration generator 71 is the one that delivers asymmetric vibration waves from the anterior chamber 21 to the solution inside the balloon 6 through the solution transport path 9 to steadily generate swirls S inside the balloon 6, with the anterior chamber 21 and the solution transport pipe 54 being communicated with each other by the T shape stopcock 51, and the solution transport pipe 54 and the vibration generator 71 being communicated with each other by the T shape stopcock 61. The solution inside the balloon 6 is vibrated and agitated by the swirls S inside the balloon 6 to keep the temperature inside the balloon 6 uniform.

Meanwhile, although there is employed the electrode 81 for delivery of radiofrequency current fixed in the vicinity of the distal end of the inner tube 3 in order to heat the inside of the balloon 6 in the present embodiment, the heating means is not limited to any particular one as long as the inside of the balloon 6 can be heated by the same. For example, the electrode 81 for delivery of radiofrequency current and the radiofrequency generator 83 may be replaced by any one set of an ultrasonic wave heating element and an ultrasonic generator; a laser heating element and a laser generator; a diode heating element and a diode power supply device; and a nichrome wire heating element and a nichrome wire power supply device.

Further, the balloon 6 is made from heat-resistant resin giving rise to no thermal deformation or the like when heating the inside of the balloon 6. As for the shape of the balloon 6, it is possible to employ other various shapes for the rotating body than the spherical shape with minor and major axes equal to each other, e.g., an oblate spheroid shape with a minor axis defined as a rotation axis, a prolate spheroid shape with a major axis defined as a rotation axis, a sand bag shape or the like. Whatever the shape of the balloon may be, however, the balloon 6 should be formed from an elastic member which is deformable when coming in close contact with an intraluminal wall.

Next is an explanation of how to use the balloon catheter system according to the present embodiment by way of practical examples. According to the present embodiment, the balloon 6 is uniformly heated to an optimal temperature by the actions of the radiofrequency delivery device 74 and the in-balloon agitation device 74, thereby enabling a target site A such as a pulmonary vein to be ablated.

Specifically, the operational piece 52 of the T shape stopcock 51 attached to the connecting pipe 15 is first operated to allow the anterior chamber 21 and the solution transport pipe 54 to communicate with each other, and then, the operational piece 62 of the T shape stopcock 61 attached to the solution transport pipe 54 is operated to allow the solution transport pipe 54 and the syringe 55 to communicate with each other. Under such conditions, the plunger 57 of the syringe 55 is pushed to thereby fill, the interior of the balloon catheter involving the catheter shaft 1 and the balloon 6 as well as the interior of the anterior tank 12 of the handle 11, with a compound solution including a physiological saline and an imaging agent having been contained in the tubular body 56 until then.

Next, the operational piece 52 of the T shape stopcock 51 is operated to allow the anterior chamber 21 and the posterior chamber 28 to communicate with each other, and the slide knob 35 is advanced to push ahead the inner shaft 3 together with the piston 27 to bring the insides of the anterior chamber 21 and the posterior chamber 28 into a negative pressure, so that the inside of the balloon 6 is vacuumed to deflate the balloon 6. In this state, the balloon catheter is then inserted into a blood vessel.

When the distal end of the balloon catheter enters the ostium of the pulmonary vein, the slide knob 35 is pulled back to bring the insides of the anterior tank 12 and posterior tank 13 into a positive pressure to inflate the balloon 6, thus allowing the balloon 6 to come in contact with the target site A. Here, when the operational piece 52 of the T shape stopcock 51 attached to the connecting pipe 15 is operated to turn the operational piece 52 in the ablation direction in which the anterior chamber 21 and the solution transport pipe 54 are allowed to communicate with each other again, the anterior tank 12 and the posterior tank 13 are disconnected to connect the anterior tank 12 with the vibration generator 71. Under such conditions, the radiofrequency delivery device 74 and the in-balloon agitation device 75 are activated, and thus, the vibration waves from the vibration generator 71 are allowed to propagate through the solution transport path 9 to agitate the inside of the balloon 6, thus allowing the radiofrequency energy from the radiofrequency generator 83 to heat the balloon 6 in a uniform manner As described above, the balloon catheter system according to the present embodiment comprises the catheter shaft 1 including the outer tube 2 and the inner tube 3 which are slidable to each other, and the deflatable or inflatable balloon 6 arranged between the distal end 4 of the outer tube 2 and the vicinity of the distal end 5 of the inner tube 3. Furthermore, the balloon catheter system is so structured as follows: the solution transport path 9 communicating with the inside of the balloon 6 is formed between the outer tube 2 and the inner tube 3; in the handle 11 of the catheter shaft 1 positioned at the proximal end of the catheter, the anterior tank 12 and the posterior tank 13 are set as the two anterior and posterior tanks connected via the connecting pipe 15; the anterior and posterior tanks 12, 13 and the inner tube 3 passing through the central portion of the tanks 12, 13 are slidable to each other; the stopcocks 22, 32 acting as a packing member for preventing the solution from leaking are located in the sliding portion between the inner tube 3 and the anterior and posterior tanks 12, 13; the anterior tank 12 and the posterior tank 13 are connected to the filling portion 8 inside the balloon 6 via the solution transport path 9; the piston 27 is provided inside the front section of the posterior tank 13; the reciprocating movement of the inner tube 3 fixed to the central portion of the piston 27 changes the inner pressures of the anterior tank 12 and the posterior tank 13; when pushing ahead the inner tube 3, the balloon 6 is allowed to stretch to make the inside of the posterior tank 13 subjected to negative pressure, thus deflating the balloon 6; contrarily, when pulling back the inner tube 3, the stretched state of the balloon 6 is released to make the inside of the posterior tank 13 subjected to positive pressure, thus inflating the balloon 6.

Conventionally, as shown in FIG. 1, operations for stretching a balloon 103 and suctioning a solution inside the balloon 103, and operations for releasing the stretched state of the balloon 103 and filling the balloon 103 with the solution were performed separately and in stages. Hence, the conventional operations would require a troublesome task and a lot of skill. According to the present embodiment, however, when pushing ahead the inner tube 3 relative to the outer tube 2, the balloon 6 is stretched and at the same time the posterior tank 13 is allowed to be subjected to a negative pressure to thereby allow the anterior tank 12, communicating with the posterior tank 13 via the connecting pipe 15, to be also subjected to a negative pressure to suction the solution inside the balloon 6, thereby deflating the balloon 6. Contrarily, when pulling back the inner tube 3 relative to the outer tube 2, the stretched state of the balloon 6 is released and at the same time the posterior tank 13 is allowed to be subjected to a positive pressure to thereby allow the anterior tank 12 also to be subjected to a positive pressure to thus fill the balloon 6 with the solution, thereby inflating the balloon 6. Hence, the operation of the balloon 6 is simplified. Accordingly, there can be provided the balloon catheter system in which the operations for stretching and deflating the balloon 6 and the operations for releasing the stretched state of the balloon 6 and inflating the same can be performed at a time with a single operation, realizing the decrease of the amount of time required for manual operations as wells as the reduction of burdens on a patient.

Further, according to the present embodiment, the balloon 6 is made from resin rich in elasticity and is formed into a rotating body shape.

As long as the balloon 2 takes the form of a rotating body shape, it can be applied to the balloon catheter system of the present embodiment, regardless of what specific shape the rotating body has. Hence, the balloon 6 can be employed for use in various applications in accordance with the shape of an intraluminal wall, for example.

Furthermore, according to the present embodiment, the piston 27 movable inside the posterior tank 13 of the handle 11 is connectable to the slide knob 35 arranged above the handle 11, thus enabling the piston 27 to be moved by a finger.

In this case, the piston 27 movable inside the posterior tank 13 can be operated by handling a terminal portion connected to the inner shaft 3, which, however, requires the handle to be switched from one hand to the other, causing troublesomeness. According to the present embodiment, the slide knob 35 is connectably provided on the handle 11, and thus the piston 27 can be operated using the slide knob 35 on the handle 11, so that a hand operation is quickened, thereby shortening the amount of time required for the operation.

Also, according to the present embodiment, the syringe 55 acting as a syringe barrel is attached to the connecting pipe 15 via the T shape stopcock 51.

This enables fine adjustment of the amount of the solution inside the balloon 6 using the syringe 55 through the switching of the T shape stopcock 51 according to need. Hence, the balloon 6 can be allowed to come in closer contact with a target organ.

Still also, according to the present embodiment, the stopcocks 22, 23 are respectively provided in the proximal ends of the anterior tank 12 and the posterior tank 13.

Thus, the stopcocks 22, 23 can be used to assist in adjustments of the piston 27 and air-bleeding operations inside the anterior and posterior tanks 12, 13.

Further, the present embodiment is configured such that the electrode 81 for delivery of radiofrequency current and the temperature sensor 82 are each provided inside the balloon 6, and then the radiofrequency energy is delivered via the lead wire 84 inside the catheter shaft 1 from the radiofrequency generator 83 provided outside the balloon catheter and at the same time the vibration waves are transmitted via the solution transport path 9 from the vibration generator 71 provided outside the balloon catheter, thereby agitating the solution inside the balloon 6.

Accordingly, due to the vibration waves transmitted from the vibration generator 71 being allowed to propagate through the solution transport path 9, the interior of the balloon 6 is agitated, and at the same time the radiofrequency energy from the radiofrequency generator 83 is delivered via the lead wire 84 to the electrode 81 for delivery of radiofrequency current, thus enabling an ablation treatment to be performed with the balloon 6 being heated in a uniform manner, thus making it possible for even a less skilled medical doctor to perform ablation treatment of cardiac dysrhythmia or cardiac valvuloplasty, easily and in a short amount of time.

Also, according to the present embodiment, there is employed such structure that allows target sites A such as mitral and aortic stenosis to be dilated by the operation for inflating the balloon 6 due to the balloon 6 being reinforced by a wire such as the guide wire 10.

Thus, when inserting the balloon 6 into a blood vessel, troubles with the balloon 6, such as bursting thereof, can be prevented, thereby enabling even a less skilled medical doctor to perform a cardiac valvuloplasty, simply and in a short time.

In the meantime, the present invention is not limited to the foregoing embodiments and various modifications are possible within the scope of the gist of the present invention. The present invention can be applied to dilate stenosed sites of luminal organs such as urethra, ureter, pancreatic duct, trachea, esophagus, intestinal canal or the like. Further, the shapes of the catheter shaft 1 and the balloon 6 are not limited to the ones shown in the foregoing embodiments but may be formed into a variety of shapes according to treatment sites.

EXPLANATION OF NUMERAL SYMBOLS 1 catheter shaft
2 outer tube
3 inner tube
6 balloon
9 solution transport path
10 guide wire (wire)
11 handle
12 anterior tank
13 posterior tank
22, 32 stopcock (packing member)
27 piston
35 slide knob
51 T shape stopcock
55 syringe (syringe barrel)
71 vibration generator
81 electrode for delivery of radiofrequency current
82 temperature sensor
83 radiofrequency generator
84 lead wire

The invention claimed is:

1. A balloon catheter system comprising:
a catheter shaft including an outer tube and an inner tube, said outer and inner tubes being slidable to each other;
an inflatable and deflatable balloon arranged between a distal end of said outer tube and a vicinity of a distal end of said inner tube;
a solution transport path formed between said outer tube and said inner tube, in communication with an inside of said balloon;
an anterior tank and a posterior tank, each tank arranged in a handle of a catheter, said anterior tank and said posterior tank being in communication with each other via a connecting pipe, said anterior tank and said posterior tank being slidable relative to said inner tube passing through central portions thereof;
a first leakproof packing member and a second leakproof packing member, said first leakproof packing member and said second leakproof packing member arranged on a first sliding portion and a second sliding portion respectively between said inner tube and each of said anterior tank and posterior tank, said anterior tank and posterior tank being allowed to communicate with an inside of said balloon via said solution transport path; and
a piston provided inside a distal section of said posterior tank to allow an inner pressure of each of said anterior tank and said posterior tank to be changed by a reciprocating movement of said inner tube fixed to a central portion of said piston,
wherein said balloon catheter system is configured such that pushing said inner tube distally allows said balloon to be stretched so that an inside of said posterior tank is subjected to a negative pressure to thereby deflate said balloon, while pulling said inner tube proximally allows the stretched state of said balloon to be released so that the inside of said posterior tank is subjected to a positive pressure to thereby inflate said balloon.

2. The balloon catheter system according to claim 1, wherein said balloon is made from an elastic resin.

3. The balloon catheter system according to claim 1, wherein said piston provided movably inside said posterior tank in said handle is connectable to a slide knob radially extending from said handle, said slide knob being movable by a finger.

4. The balloon catheter system according to claim 1, wherein a syringe barrel is attached to said connecting pipe via a T shape stopcock.

5. The balloon catheter system according to claim 1, wherein said first leakproof packing member and said second leakproof packing member are a first stopcock and a second stopcock provided on respective proximal end portions of said anterior tank and said posterior tank.

6. The balloon catheter system according to claim 1, further comprising:
an electrode for delivery of a radiofrequency current;
a temperature sensor;
a radiofrequency generator configured to deliver a radiofrequency energy via a lead wire inside said catheter shaft; and
a vibration generator configured to transmit vibration waves via said solution transport path for agitating a solution inside said balloon,
wherein said electrode for delivery of a radiofrequency current and said temperature sensor are provided inside said balloon.

7. The balloon catheter system according to claim 1, wherein said balloon is wire-reinforced and configured to inflate so as to enable a mitral or an aortic stenosis to dilate.

8. The balloon catheter system according to claim 2, wherein said piston provided movably inside said posterior tank in said handle is connectable to a slide knob radially extending from said handle, said slide knob being movable by a finger.

9. The balloon catheter system according to claim 2, wherein a syringe barrel is attached to said connecting pipe via a T shape stopcock.

10. The balloon catheter system according to claim 2, wherein said first leakproof packing member and said second leakproof packing member are a first stopcock and a second stopcock provided on respective proximal end portions of said anterior tank and said posterior tank.

11. The balloon catheter system according to claim 2, further comprising:
an electrode for delivery of a radiofrequency current;
a temperature sensor;
a radiofrequency generator configured to deliver a radiofrequency energy via a lead wire inside said catheter shaft; and
a vibration generator configured to transmit vibration waves via said solution transport path for agitating a solution inside said balloon,
wherein said electrode for delivery of a radiofrequency current and said temperature sensor are provided inside said balloon.

12. The balloon catheter system according to claim 2, wherein said balloon is wire-reinforced and configured to inflate so as to enable a mitral or an aortic stenosis to dilate.

13. The balloon catheter system according to claim 3, wherein a syringe barrel is attached to said connecting pipe via a T shape stopcock.

14. The balloon catheter system according to claim 3, wherein said first leak roof packing member and said second leak roof packing member are a first stopcock and a second stopcock provided on respective proximal end portions of said anterior tank and said posterior tank.

15. The balloon catheter system according to claim 3, further comprising:
an electrode for delivery of a radiofrequency current;
a temperature sensor;
a radiofrequency generator configured to deliver a radiofrequency energy via a lead wire inside said catheter shaft; and
a vibration generator configured to transmit vibration waves via said solution transport path for agitating a solution inside said balloon,
wherein said electrode for delivery of a radiofrequency current and said temperature sensor are provided inside said balloon.

16. The balloon catheter system according to claim 3, wherein said balloon is wire-reinforced and configured to inflate so as to enable a mitral or an aortic stenosis to dilate.

17. The balloon catheter system according to claim 4, wherein said first leakproof packing member and said second leakproof packing member are a first stopcock and a second stopcock provided on respective proximal end portions of said anterior tank and said posterior tank.

18. The balloon catheter system according to claim 4, further comprising:
an electrode for delivery of a radiofrequency current;
a temperature sensor;
a radiofrequency generator delivering a radiofrequency energy via a lead wire inside said catheter shaft; and
a vibration generator transmitting vibration waves via said solution trans sort path for agitating a solution inside said balloon,
wherein said electrode for delivery of a radiofrequency current and said temperature sensor are provided inside said balloon.

19. The balloon catheter system according to claim 4, wherein said balloon is wire-reinforced and configured to inflate so as to enable a mitral or an aortic stenosis to dilate.

20. The balloon catheter system according to claim 5, further comprising:
an electrode for delivery of a radiofrequency current;
a temperature sensor;
a radiofrequency generator configured to deliver a radiofrequency energy via a lead wire inside said catheter shaft; and
a vibration generator configured to transmit vibration waves via said solution transport path for agitating a solution inside said balloon,
wherein said electrode for delivery of a radiofrequency current and said temperature sensor are provided inside said balloon.

21. The balloon catheter system according to claim 5, wherein said balloon is wire-reinforced and configured to inflate so as to enable a mitral or an aortic stenosis to dilate.

22. The balloon catheter system according to claim 6, wherein said balloon is wire-reinforced and configured to inflate so as to enable a mitral or an aortic stenosis to dilate.

* * * * *